US012532925B1

(12) United States Patent
Qi et al.

(10) Patent No.: US 12,532,925 B1
(45) Date of Patent: Jan. 27, 2026

(54) ABDOMINAL SUPPORT BELT

(71) Applicant: Shenzhen Lute Jiacheng Supply Chain Management Co., Ltd., Guangdong (CN)

(72) Inventors: Zijuan Qi, Guangdong (CN); Ping Yan, Guangdong (CN)

(73) Assignee: Shenzhen Lute Jiacheng Supply Chain Management Co., Ltd., Shenzhen (CN)

( * ) Notice: Subject to any disclaimer, the term of this patent is extended or adjusted under 35 U.S.C. 154(b) by 0 days.

(21) Appl. No.: 19/096,769

(22) Filed: Apr. 1, 2025

(30) Foreign Application Priority Data

Mar. 11, 2025 (CN) ......................... 202520422316.3

(51) Int. Cl.
*A41C 1/10* (2006.01)
*A41F 9/02* (2006.01)
*A61F 5/02* (2006.01)

(52) U.S. Cl.
CPC .................. *A41C 1/10* (2013.01); *A41F 9/02* (2013.01); *A61F 5/028* (2013.01)

(58) Field of Classification Search
CPC .................................. A41F 9/02; A61F 5/028
See application file for complete search history.

(56) References Cited

U.S. PATENT DOCUMENTS 1,857,179 A * 5/1932 Bowman ................. A61F 5/449 450/155
5,188,585 A * 2/1993 Peters ..................... A61F 5/028 2/311
5,445,601 A * 8/1995 Harlow ................... A61F 5/028 128/845
2007/0037483 A1* 2/2007 Huang ..................... A41C 1/10 450/151
2014/0221892 A1* 8/2014 Javaid ..................... A61F 5/028 602/19

OTHER PUBLICATIONS

Mood Fabrics; "Tips & Tricks for Sewing with Velcro"; Mar. 11, 2021 https://www.moodfabrics.com/blog/tips-tricks-for-sewing-with-velcro/ (Year: 2021).*

* cited by examiner

*Primary Examiner* — Jocelyn Bravo

(57) ABSTRACT

The present disclosure provides an abdominal support belt comprising: a waist support portion configured to extend across a user's waist region and along both sides of the user when worn; and an abdominal support portion connected to the waist support portion and configured to be positioned over the user's abdominal region when worn, wherein the abdominal support portion includes a first strap and a second strap extending respectively along both sides of the waist support portion, wherein the first strap and the second strap are detachably connected, and wherein the first strap and the second strap have unequal lengths.

14 Claims, 3 Drawing Sheets

ABDOMINAL SUPPORT BELT

CROSS-REFERENCE TO RELATED APPLICATIONS

The present application claims priority to Chinese Patent Application No. 202520422316.3, filed on Mar. 11, 2025, the entire contents of which are incorporated herein by reference.

TECHNICAL FIELD

The present application relates to the technical field of maternal and baby products, particularly to an abdominal support belt.

BACKGROUND

An abdominal support belt for pregnant women, serving as a critical auxiliary device during pregnancy, has core functions of distributing abdominal weight, reducing lumbar strain, and maintaining body balance. Conventional abdominal support belts typically adopt front-closure or back-closure designs, such as using hook-and-loop fasteners, hooks, or straps for fixation at the abdominal front or back.

Such designs face multiple practical limitations: First, front-closure structures require users to bend forward or twist sideways to adjust fixation points due to the protrusion of the abdominal region, posing significant difficulty for late-term pregnant women with restricted mobility. This process is not only cumbersome but may also cause abdominal compression or insecure fixation due to improper posture. Second, while back-closure designs avoid direct interference with the abdomen, their dorsal fixation points necessitate assistance from others for donning, substantially compromising user autonomy and convenience. Furthermore, existing belts generally lack dynamic adaptability to effectively conform to continuously changing abdominal and lumbar contours throughout pregnancy progression. During prolonged activity or postural changes, these belts frequently exhibit issues such as strap displacement, loosening, or localized pressure concentration, resulting in unstable support and potential skin irritation. Additionally, most products provide limited adjustability through single-mechanism designs, failing to achieve precise pressure distribution tailored to varying body types or gestational stages, thereby further restricting comfort and functionality.

Thus, there is an urgent need for an abdominal support belt design that simplifies donning procedures, enables independent operation, and incorporates dynamic conformity with flexible adjustability, thereby addressing the significant deficiencies of conventional products in usability, adaptability, and user experience.

SUMMARY

In view of the shortcomings of the prior art, an embodiment of the present application provides an abdominal support belt that facilitates user operation and ensures a close fit with the user's body.

To address the above technical problems, one embodiment of the present application provides an abdominal support belt, comprising: a waist support portion configured to extend across a user's waist region and along both sides of the user when worn; and an abdominal support portion connected to the waist support portion and configured to be positioned over the user's abdominal region when worn, wherein the abdominal support portion includes a first strap and a second strap extending respectively along both sides of the waist support portion, wherein the first strap and the second strap are detachably connected, and wherein the first strap and the second strap have unequal lengths.

In one embodiment, at least a portion of the abdominal support belt is made of a sheet material comprising an outer layer, an inner layer, and an adhesive layer disposed between the outer layer and the inner layer.

In one embodiment, the adhesive layer comprises a first adhesive layer, a cushion layer, and a second adhesive layer sequentially stacked from the inner layer toward the outer layer.

In one embodiment, the first adhesive layer and the second adhesive layer comprise adhesive material.

In one embodiment, the cushion layer comprises a sponge layer.

In one embodiment, the inner layer defines a plurality of ventilation holes.

In one embodiment, the first strap has a length greater than a length of the second strap.

In one embodiment, the first strap comprises a side panel extending along a lateral side of the user's abdomen when worn, and an abdominal panel extending along the user's abdomen when worn, wherein the abdominal panel has a thickness greater than a thickness of the side panel.

In one embodiment, the side panel and the abdominal panel are joined by stitching.

In one embodiment, the second strap includes a lifting handle.

In one embodiment, the waist support portion is embedded with a support structure, wherein the support structure has a hardness greater than a hardness of adjacent portions of the waist support portion.

In one embodiment, the support structure comprises a plurality of support strips spaced apart from one another.

In one embodiment, each support strip extends along a vertical direction of the user when the belt is worn, and wherein each support strip tapers in thickness from a central region toward opposing ends.

In one embodiment, an upper edge of each support strip is arcuate.

In one embodiment, a lower edge of the waist support portion is linear at least at a region corresponding to the user's back.

In one embodiment, the first strap extends across the user's abdominal region when worn and is detachably connected to the second strap at a lateral side of the user.

In one embodiment, a central portion of the abdominal panel has a width greater than widths of end portions of the abdominal panel.

In one embodiment, a lower edge of the first strap extends obliquely upward from the abdominal region to a junction between the first strap and the second strap when worn.

In one embodiment, a lower edge of the second strap extends obliquely downward from the waist region to a junction between the second strap and the first strap when worn.

In one embodiment, the first strap and the second strap are connected via a hook-and-loop fastener, wherein one of the first strap or the second strap includes a loop surface, and the other includes a hook surface.

In one embodiment, the hook-and-loop fastener on the second strap has an adjustable length to permit positional adjustment of the detachable connection between the first strap and the second strap.

In one embodiment, the hook-and-loop fastener is secured to the first strap or the second strap by stitching, wherein the stitching comprises peripheral stitching along edges of the hook-and-loop fastener, and intermediate stitching within a central region of the hook-and-loop fastener.

To address the above technical problems, another embodiment of the present application provides an abdominal support belt, comprising: a waist support portion configured to extend across a user's waist region and along both sides of the user when worn; and an abdominal support portion connected to the waist support portion and configured to be positioned over the user's abdominal region when worn, wherein the abdominal support portion includes a first strap and a second strap extending respectively along both sides of the waist support portion, wherein the first strap and the second strap are detachably connected, and wherein the first strap extends across the user's abdominal region when worn and is detachably connected to the second strap at a lateral side of the user.

In one embodiment, at least a portion of the abdominal support belt is made of a sheet material comprising an outer layer, an inner layer, and an adhesive layer disposed between the outer layer and the inner layer.

In one embodiment, the adhesive layer comprises a first adhesive layer, a cushion layer, and a second adhesive layer sequentially stacked from the inner layer toward the outer layer.

In one embodiment, the first adhesive layer and the second adhesive layer comprise adhesive material.

In one embodiment, the cushion layer comprises a sponge layer.

In one embodiment, the inner layer defines a plurality of ventilation holes.

In one embodiment, the first strap has a length greater than a length of the second strap.

In one embodiment, the first strap comprises a side panel extending along a lateral side of the user's abdomen when worn, and an abdominal panel extending along the user's abdomen when worn, wherein the abdominal panel has a thickness greater than a thickness of the side panel.

In one embodiment, the side panel and the abdominal panel are joined by stitching.

In one embodiment, the second strap includes a lifting handle.

In one embodiment, the waist support portion is embedded with a support structure, wherein the support structure has a hardness greater than a hardness of adjacent portions of the waist support portion.

In one embodiment, the support structure comprises a plurality of support strips spaced apart from one another.

In one embodiment, each support strip extends along a vertical direction of the user when the belt is worn, and wherein each support strip tapers in thickness from a central region toward opposing ends.

In one embodiment, an upper edge of each support strip is arcuate.

In one embodiment, a lower edge of the waist support portion is linear at least at a region corresponding to the user's back.

In one embodiment, a central portion of the abdominal panel has a width greater than widths of end portions of the abdominal panel.

In one embodiment, a lower edge of the first strap extends obliquely upward from the abdominal region to a junction between the first strap and the second strap when worn.

In one embodiment, a lower edge of the second strap extends obliquely downward from the waist region to a junction between the second strap and the first strap when worn.

In one embodiment, the first strap and the second strap are connected via a hook-and-loop fastener, wherein one of the first strap or the second strap includes a loop surface, and the other includes a hook surface.

In one embodiment, the hook-and-loop fastener on the second strap has an adjustable length to permit positional adjustment of the detachable connection between the first strap and the second strap.

In one embodiment, the hook-and-loop fastener is secured to the first strap or the second strap by stitching, wherein the stitching comprises peripheral stitching along edges of the hook-and-loop fastener, and intermediate stitching within a central region of the hook-and-loop fastener.

The embodiments of the present application provide an abdominal support belt comprising: a waist support portion configured to extend across a user's waist region and along both sides of the user when worn; and an abdominal support portion connected to the waist support portion and configured to be positioned over the user's abdominal region when worn, wherein the abdominal support portion includes a first strap and a second strap extending respectively along both sides of the waist support portion, wherein the first strap and the second strap are detachably connected, and wherein the first strap and the second strap have unequal lengths, thereby allowing the user to open and close the belt at a lateral side of the body or an adjacent position to facilitate user operation.

BRIEF DESCRIPTION OF THE DRAWINGS

To more clearly illustrate the technical solutions in the embodiments of the present application or the prior art, the following provides a brief description of the accompanying drawings required for describing the embodiments or the prior art. It is evident that the drawings in the following description are merely some embodiments of the present application, and other drawings can be obtained by those of ordinary skill in the art based on the structures shown in these drawings without creative effort.

The implementation, functional features, and advantages of the present application will be further described in conjunction with the embodiments and with reference to the accompanying drawings.

DETAILED DESCRIPTION OF THE EMBODIMENTS

In the present application, the terms "arranged," "provided with," and "connected" should be understood broadly. For example, a connection may be fixed, detachable, or integrally constructed; it may be mechanical or electrical; it may be direct or indirectly connected through an intermediary, or it may refer to internal communication between two devices, components, or constituent parts. Those of ordinary skill in the art can understand the specific meanings of these terms in the context of the present application based on specific circumstances.

The terms "center," "longitudinal," "transverse," "length," "width," "thickness," "upper," "lower," "front," "rear," "left," "right," "vertical," "horizontal," "top," "bottom," "inner," "outer," "radial," and "circumferential" are used to describe orientations or positional relationships based on the orientations or positional relationships shown in the accompanying drawings. These terms are used solely for the purpose of facilitating the description of the present application and simplifying the description, and do not indicate or imply that the referenced devices or components must have a specific orientation or be constructed and operated in a specific orientation. Therefore, these terms should not be construed as limiting the present application.

Furthermore, the terms "first" and "second" are used for descriptive purposes only and should not be construed as indicating or implying relative importance or implicitly specifying the quantity of the indicated technical features. Thus, features defined by "first" or "second" may explicitly or implicitly include at least one such feature. In the description of the present application, the term "plurality" means at least two, such as two, three, etc., unless explicitly stated otherwise.

Additionally, some of the above terms may be used to indicate meanings other than orientation or positional relationships. For example, the term "upper" may, in some cases, also be used to indicate a certain dependency or connection relationship. Those of ordinary skill in the art can understand the specific meanings of these terms in the context of the present application based on specific circumstances.

Figure 1:
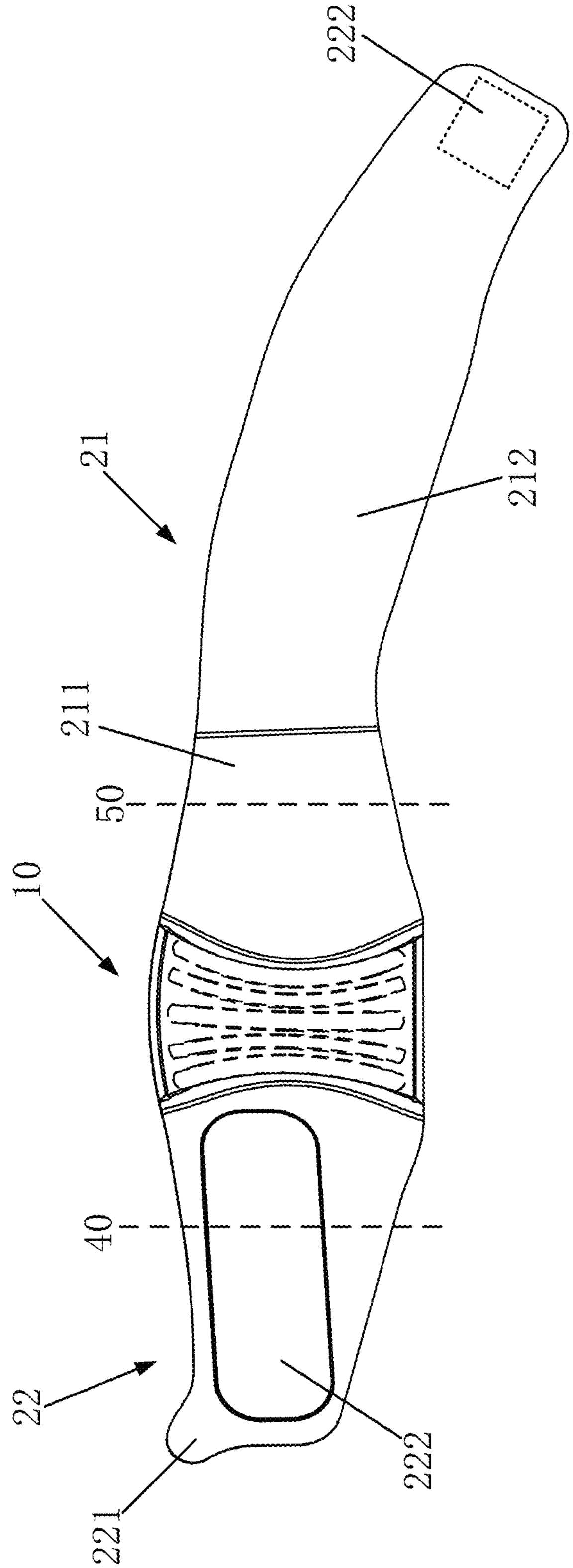
FIG. 1 is a schematic structural diagram of an abdominal support belt in an unfolded state according to an embodiment of the present application.
Figure 2:
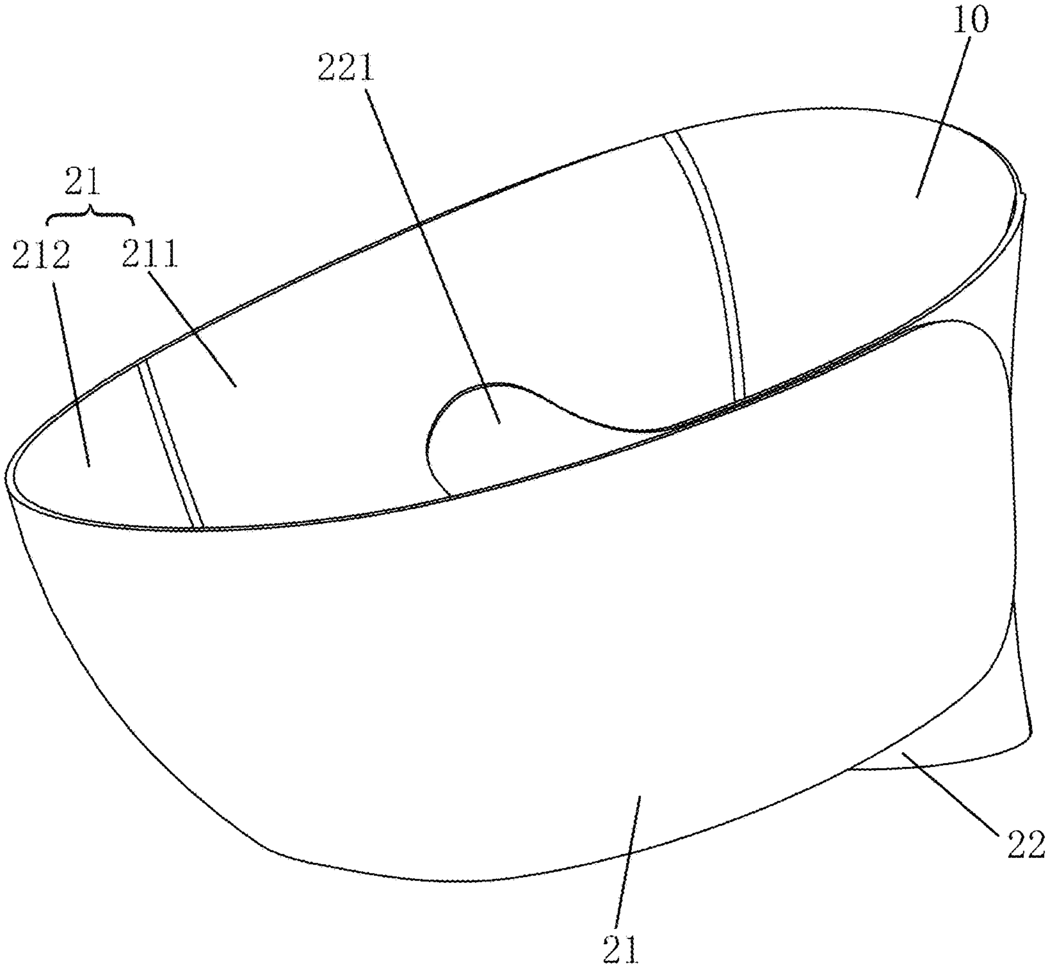
FIG. 2 is a schematic structural diagram of the abdominal support belt in a worn state according to an embodiment of the present application.

Please refer to FIG. 1 and FIG. 2. FIG. 1 is a schematic structural diagram of an abdominal support belt in an unfolded state according to an embodiment of the present application; FIG. 2 is a schematic structural diagram of the abdominal support belt in a worn state according to an embodiment of the present application.

The abdominal support belt of the present embodiment comprises: a waist support portion 10 and an abdominal support portion (not labeled). The waist support portion 10 is configured to extend across a user's waist region and along both sides of the user when worn.

As shown in FIG. 1 and FIG. 2, the abdominal support portion is connected to the waist support portion 10 and is configured to be positioned over the user's abdominal region when worn. The abdominal support portion includes a first strap 21 and a second strap 22 extending respectively along both sides of the waist support portion 10. The first strap 21 and the second strap 22 are detachably connected, and the first strap 21 and the second strap 22 have unequal lengths.

As shown in FIG. 2, the abdominal support portion and the waist support portion 10 may be integrally formed, cut from the same sheet material, or joined by stitching, or may be detachably connected. Dashed line 40 and dashed line 50 approximately correspond to the positions of the two side seams of the human body when the belt is worn. For example, dashed line 40 corresponds to the left side seam of the human body, and dashed line 50 corresponds to the right side seam of the human body. The portion to the left of dashed line 40 is the second strap 22, the portion between dashed line 40 and dashed line 50 is the waist support portion 10, and the portion to the right of dashed line 50 is the first strap 21.

In the embodiment of the present application, by configuring the first strap 21 and the second strap 22 of the abdominal support portion to have unequal lengths, the user can conveniently open and close the belt at a lateral side of the body or a position adjacent to the abdominal side, making the operation more convenient. This is particularly beneficial for pregnant women with larger abdomens, as side closure is easier to manage. Additionally, when the first strap has a greater length, it provides a larger overall wrapping effect for the abdominal region. Furthermore, detaching the belt at the side, as opposed to the front of the abdomen, reduces pressure on the abdomen, thereby enhancing comfort.

As shown in FIG. 2, in one embodiment, the first strap 21 has a length greater than that of the second strap 22. The first strap 21 extends along the right side of the user to the abdominal region when worn, and the second strap 22 extends along the left side of the user to the abdominal region when worn. In other embodiments, the first strap may have a length less than that of the second strap, which is not limited in the embodiments of the present application.

As shown in FIG. 2, in one embodiment, the first strap 21 includes a side panel 211 and an abdominal panel 212. The side panel 211 extends along a lateral side of the user's abdomen when worn, and the abdominal panel 212 extends along the user's abdomen when worn. The abdominal panel 212 has a thickness greater than that of the side panel 211. This design ensures sufficient cushioning of the abdominal panel 212 while maintaining adequate breathability of the side panel 211. Additionally, by configuring the abdominal panel 212 to be thicker, stronger support can be provided in the central abdominal region to distribute weight, whereas the side panel 211, being thinner, maintains flexibility for lateral movement and avoids a sense of constraint.

In one embodiment, the hook-and-loop fastener 222 is secured to the first strap 21 or the second strap 22 by stitching. The stitching includes peripheral stitching along the edges of the hook-and-loop fastener and intermediate stitching within a central region of the hook-and-loop fastener. The peripheral stitching is sewn along the four sides of the hook-and-loop fastener 222, while the intermediate stitching is arranged in an "8" shape, "X" shape, or parallel lines across the central portion of the hook-and-loop fastener 222. This dual fixation prevents the hook-and-loop fastener from peeling or detaching after repeated use, thereby extending its service life.

Figure 3:
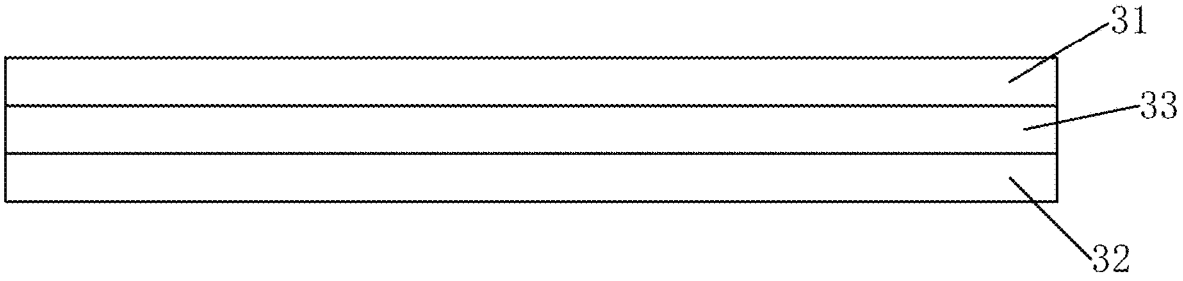
FIG. 3 is a schematic diagram of a layered structure of a sheet material according to an embodiment of the present application.

As shown in FIG. 3, which is a schematic diagram of a layered structure of a sheet material according to an embodiment of the present application, in one embodiment, at least a portion of the abdominal support belt is made of a sheet material 30. The sheet material 30 comprises an outer layer 31, an inner layer 32, and an adhesive layer 33 disposed between the outer layer 31 and the inner layer 32.

In the embodiment of the present application, the abdominal support belt is designed and manufactured such that the sheet material 30 includes the outer layer 31, the inner layer 32, and the adhesive layer 33 disposed between the outer layer 31 and the inner layer 32, enabling the sheet material to be freely cut into irregular shapes. Specifically, the adhesive layer tightly bonds the material layers together, ensuring no risk of delamination during cutting, thereby allowing the abdominal support belt to be tailored into curved, wavy, or irregular-edged contours based on ergonomic requirements. This design enables the abdominal support belt to more precisely conform to the physiological curves of the pregnant user's waist and abdominal regions. For example, the lower edge of the waist support portion 10 may be cut straight to fit the flat area of the back, while the edges of the abdominal support portion may be cut at an incline or curve to accommodate the protruding abdominal shape. Additionally, this layered structure of the sheet material 30 ensures that the abdominal support belt remains lightweight and discreet while providing strong elasticity and support.

Figure 4:
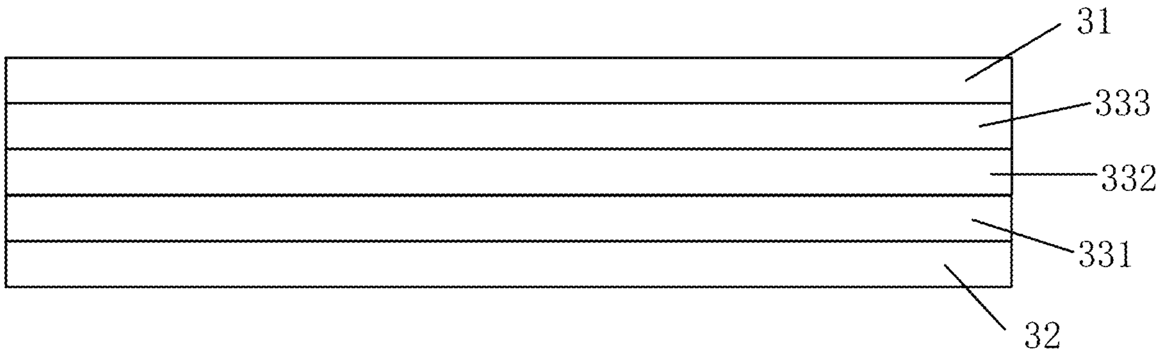
FIG. 4 is a schematic diagram of a layered structure of a sheet material according to another embodiment of the present application.

As shown in FIG. 4, which is a schematic diagram of a layered structure of a sheet material according to another embodiment of the present application, in one embodiment, the adhesive layer 33 comprises a first adhesive layer 331, a cushion layer 332, and a second adhesive layer 333 sequentially stacked from the inner layer toward the outer layer. This layered adhesive approach ensures the structural strength of the sheet material while utilizing the cushion layer to provide flexible cushioning space, reducing the rigid pressure sensation on the waist and abdominal regions during wear.

In one embodiment, the first adhesive layer 331 and the second adhesive layer 333 are adhesive layers. The adhesive layers may be made of hot-melt adhesive or eco-friendly adhesives, bonded to adjacent layers through heat pressing or coating processes, ensuring tight integration between the layers of the sheet material without gaps. This prevents structural loosening or deformation caused by delamination.

In one embodiment, the cushion layer 332 is a sponge layer. The sponge layer is made of high-resilience, breathable polyurethane foam or memory foam. Its porous structure further absorbs localized pressure fluctuations during movement while enhancing the breathability of the sheet material, reducing heat buildup.

In one embodiment, the inner layer 32 is provided with ventilation holes. The ventilation holes are distributed in an array pattern on the inner layer, with hole size and density designed according to ergonomic requirements. By increasing airflow pathways, the ventilation holes accelerate sweat evaporation, preventing skin discomfort caused by heat and moisture accumulation during prolonged wear.

As shown in FIG. 1 and FIG. 2, an embodiment of the present application further provides an abdominal support belt. The abdominal support belt comprises: a waist support portion 10 configured to extend across a user's waist region and along both sides of the user when worn; and an abdominal support portion connected to the waist support portion 10 and configured to be positioned over the user's abdominal region when worn. The abdominal support portion includes a first strap 21 and a second strap 22 extending respectively along both sides of the waist support portion 10. The first strap 21 and the second strap 22 are detachably connected, and the first strap 21 extends across the user's abdominal region when worn and is detachably connected to the second strap 22 at a lateral side of the user.

In one embodiment, the abdominal support belt includes the waist support portion 10 and the abdominal support portion. The waist support portion 10 is configured to extend across the user's waist region and along both sides of the user when worn. Its width and length are designed based on the dimensions of the human waist to fully cover the lumbar region and provide uniform circumferential support. Both sides of the waist support portion 10 are connected to the first strap 21 and the second strap 22 of the abdominal support portion, forming an integrated support structure.

The abdominal support portion is configured to be positioned over the user's abdominal region when worn and includes the first strap 21 and the second strap 22 extending respectively along both sides of the waist support portion 10. The first strap 21 extends from one side of the waist support portion 10 and passes through the user's abdominal region, while the second strap 22 extends from the other side of the waist support portion 10 to the lateral side of the user. The two straps are fixed at the lateral side through a detachable connection structure (such as a hook-and-loop fastener, hook, or snap button). This lateral connection design allows the user to operate the belt without bending over or requiring assistance, making it particularly suitable for pregnant women with limited mobility in the late stages of pregnancy.

When worn, the first strap 21 extends from the central abdominal region to the lateral side, covering the main protruding area of the abdomen to provide support, while the second strap 22 extends along the lateral side to the connection point with the first strap 21. By adjusting the connection position between the first strap 21 and the second strap 22, the user can customize the tightness based on their waist and abdominal size, ensuring a snug fit and even pressure distribution. Additionally, the detachable connection structure of the first strap 21 and the second strap 22 facilitates quick donning and removal while allowing dynamic adjustments to adapt to changes in waist and abdominal shape during pregnancy.

The above design achieves comprehensive support and dynamic adaptation to the waist and abdominal regions through the segmented connection of the waist support portion 10 and the abdominal support portion, as well as the lateral fixation mechanism. This addresses the issues of inconvenient wear, difficulty in adjustment, and inadequate fit associated with traditional abdominal support belts.

The embodiments of the present application provide an abdominal support belt comprising: a waist support portion configured to extend across a user's waist region and along both sides of the user when worn; and an abdominal support portion connected to the waist support portion and configured to be positioned over the user's abdominal region when worn. The abdominal support portion includes a first strap and a second strap extending respectively along both sides of the waist support portion. The first strap and the second strap are detachably connected, and the first strap and the second strap have unequal lengths, allowing the user to conveniently open and close the belt at a lateral side of the body or an adjacent position, thereby facilitating user operation.

To make the objectives, technical solutions, and advantages of the present application clearer, the following further describes the present application in detail with reference to the accompanying drawings and embodiments. It should be understood that the specific embodiments described herein are merely intended to explain the present application and are not intended to limit the present application.

The above descriptions are only specific implementations of the present application. It should be noted that, for those of ordinary skill in the art, various modifications and refinements can be made without departing from the principles of the present application. These modifications and refinements should also be regarded as falling within the protection scope of the present application.

What is claimed is:

1. An abdominal support belt, comprising:

a waist support portion configured to extend across a user's waist region and along both sides of the user when worn; and an abdominal support portion connected to the waist support portion and configured to be positioned over the user's abdominal region when worn, the abdominal support portion comprising a first strap and a second strap extending respectively along both sides of the waist support portion, wherein the first strap and the second strap are detachably connected, the first strap and the second strap have unequal lengths, and the first strap has a length greater than a length of the second strap, wherein the first strap comprises a side panel extending along a lateral side of the user's abdomen when worn, and an abdominal panel extending along the user's abdomen when worn, wherein the abdominal panel has a thickness greater than a thickness of the side panel, and a central portion of the abdominal panel has a width greater than widths of end portions of the abdominal panel.

2. The abdominal support belt of claim 1, wherein at least a portion of the belt is formed from a sheet material comprising an outer layer, an inner layer, and an adhesive layer disposed between the outer layer and the inner layer.

3. The abdominal support belt of claim 2, wherein the adhesive layer comprises a first adhesive layer, a cushion layer, and a second adhesive layer sequentially stacked from the inner layer toward the outer layer.

4. The abdominal support belt of claim 3, wherein the cushion layer comprises a sponge layer.

5. The abdominal support belt of claim 1, wherein the side panel and the abdominal panel are joined by stitching.

6. The abdominal support belt of claim 1, wherein the second strap includes a lifting handle.

7. The abdominal support belt of claim 1, wherein the waist support portion is embedded with a support structure, wherein the support structure has a hardness greater than a hardness of adjacent portions of the waist support portion.

8. The abdominal support belt of claim 1, wherein a lower edge of the waist support portion is linear at least at a region corresponding to the user's back.

9. The abdominal support belt of claim 1, wherein the first strap extends across the user's abdominal region when worn and is detachably connected to the second strap at a lateral side of the user.

10. The abdominal support belt of claim 1, wherein a lower edge of the first strap extends obliquely upward from the abdominal region to a junction between the first strap and the second strap when worn.

11. The abdominal support belt of claim 1, wherein the first strap and the second strap are connected via a hook-and-loop fastener, wherein one of the first strap or the second strap includes a loop surface, and the other includes a hook surface.

12. The abdominal support belt of claim 11, wherein the hook-and-loop fastener is configured to permit positional adjustment of the detachable connection between the first strap and the second strap, such that a wearing length of the abdominal support belt may be adjusted.

13. The abdominal support belt of claim 11, wherein the hook-and-loop fastener is secured to the first strap or the second strap by stitching, wherein the stitching comprises peripheral stitching along edges of the hook-and-loop fastener, and intermediate stitching within a central region of the hook-and-loop fastener.

14. An abdominal support belt, comprising:

a waist support portion configured to extend across a user's waist region and along both sides of the user when worn; and an abdominal support portion connected to the waist support portion and configured to be positioned over the user's abdominal region when worn, the abdominal support portion comprising a first strap and a second strap extending respectively along both sides of the waist support portion, wherein the first strap and the second strap are detachably connected, wherein the first strap extends across the user's abdominal region when worn and is detachably connected to the second strap at a lateral side of the user, and wherein the first strap has a length greater than a length of the second strap, wherein the first strap comprises a side panel extending along a lateral side of the user's abdomen when worn, and an abdominal panel extending along the user's abdomen when worn, wherein the abdominal panel has a thickness greater than a thickness of the side panel, and a central portion of the abdominal panel has a width greater than widths of end portions of the abdominal panel.

* * * * *